United States Patent
Franzke et al.

(10) Patent No.: US 8,680,333 B2
(45) Date of Patent: Mar. 25, 2014

(54) PROCESS FOR THE PREPARATION OF AROMATIC FORMAMIDES

(75) Inventors: Axel Franzke, Mannheim (DE); Torsten Mattke, Freinsheim (DE); Julia Leschinski, Mannheim (DE); Radwan Abdallah, Ludwigshafen (DE); Michael Bock, Ruppertsberg (DE); Robert Baumann, Mannheim (DE); Eckhard Stroefer, Mannheim (DE)

(73) Assignee: BASF SE, Ludwigshafen (DE)

( * ) Notice: Subject to any disclaimer, the term of this patent is extended or adjusted under 35 U.S.C. 154(b) by 85 days.

(21) Appl. No.: 13/513,752

(22) PCT Filed: Dec. 1, 2010

(86) PCT No.: PCT/EP2010/068621
§ 371 (c)(1),
(2), (4) Date: Jun. 4, 2012

(87) PCT Pub. No.: WO2011/067278
PCT Pub. Date: Jun. 9, 2011

(65) Prior Publication Data
US 2012/0253072 A1 Oct. 4, 2012

(30) Foreign Application Priority Data
Dec. 4, 2009 (EP) .................................... 09178057

(51) Int. Cl.
*C07C 231/02* (2006.01)
*C07C 233/03* (2006.01)

(52) U.S. Cl.
USPC ........................... 564/134; 564/135; 564/218

(58) Field of Classification Search
USPC .......................................... 564/134, 135, 218
See application file for complete search history.

(56) References Cited

U.S. PATENT DOCUMENTS

| | | | |
|---|---|---|---|
| 4,258,200 A | | 3/1981 | Daughenbaugh |
| 7,268,255 B2 * | | 9/2007 | Kampfen et al. ............. 564/218 |
| 2005/0027120 A1 | | 2/2005 | Gojon-Zorrilla |

FOREIGN PATENT DOCUMENTS

| | | |
|---|---|---|
| DE | 138839 | 6/1902 |
| DE | 38 32 571 | 5/1990 |

OTHER PUBLICATIONS

Daszkiewicz, Z., et al., "A Simple Route to N-Methylarylamines," Chemical Papers, vol. 47, No. 2, pp. 109-113, (1993).
Lewin, A.H., et al., "Galanthamine analogs: 6H-benzofuro[3a,3,2,-e,f][1]benzazepine arid 6H-benzofuro[3a,3,2-e,f][3]benzazepine," Tetrahedron, vol. 61, pp. 7144-7152, (2005).
Ishii, Y., et al., "Acylation of Alcohols and Amines with Vinyl Acetates Catalyzed by Cp*$_2$Sm(thf)$_2$," Journal of Organic Chemistry, vol. 61, pp. 3088-3092, (1996).
Casanova, J., et al., "The Isonitrile-Nitrile Isomerization," Journal of Organic Chemistry, vol. 31, pp. 3473-3482, (1966).
Maya, F., et al., "Synthesis of terphenyl oligomers as molecular electronic device candidates," Tetrahedron, vol. 60, pp. 81-92, (2004).
Jung, S.H., et al., "A Practical and Convenient Procedure for the N-Formylation of Amines Using Formic Acid," Bulletin of the Korean Chemical Society, vol. 23, No. 1, pp. 149-150, (2002).
Kisfaludy, L., et al., "Rapid and Selective Formylation With Pentafluorophenyl Formate," Synthesis, p. 510, (1987).
Hill, D.R., et al., "2,2,2-Trifluoroethyl Formate: A Versatile and Selective Reagent for the Formylation of Alcohols, Amines, and N-Hydroxylamines," Organic Letters, vol. 4, No. 1, pp. 111-113, (2002).
Lygin, A.V., et al., "ortho-Lithiophenyl Isocyanide: A Versatile Precursor for 3H-Quinazolin-4-ones and 3H-Quinazolin-4-thiones," Organic Letters, vol. 11, No. 2, pp. 389-392, (2009).
Janza, B., et al., "Isonitrile Trapping Reactions under Thermolysis of Alkoxyamines for the Synthesis of Quinolines," Organic Letters, vol. 8, No. 9, pp. 1875-1878, (2006).
International Search Report Issued Feb. 25, 2011 in PCT/EP10/68621 Filed Dec. 1, 2010.
U.S. Appl. No. 13/479,961, filed May 24, 2012, Stroefer, et al.

* cited by examiner

*Primary Examiner* — Shailendra Kumar
(74) *Attorney, Agent, or Firm* — Oblon, Spivak, McClelland, Maier & Neustadt, L.L.P.

(57) ABSTRACT

The invention relates to a process for the preparation of formamides by reacting aromatic amines with a formic acid ester in the presence of a catalyst, wherein the catalyst is a phosphorus-containing acid or a Lewis-acidic metal salt.

20 Claims, No Drawings

PROCESS FOR THE PREPARATION OF AROMATIC FORMAMIDES

This application is a 371 of PCT/EP10/68621, filed Dec. 1, 2010.

The invention relates to a process for the preparation of aromatic formamides by reacting mono-, di- or polyfunctional aromatic amines with a formic acid ester in the presence of catalytic amounts of a phosphorus-containing acid or a Lewis-acidic metal salt, with high selectivities and yields being achieved even after short reaction times. The formamides prepared in this way can be converted subsequently to industrially important isocyanates.

The thermal reaction of aliphatic amines with methyl formate to give the corresponding formamides can be carried out with very good selectivities and space-time yields and is also used on an industrial scale, for example for the production of N,N-dimethylformamide (DMF) (Industrielle Organische Chemie, Wiley-VCH, Weinheim, 2007 (6), 49). An analogous transformation of aromatic amines to give the respective formamides, by contrast, is considerably less efficient on account of the reduced nucleophilicity of these amines. Here, even after long reaction times, only unsatisfactory conversions and yields are achieved, which hinder a potential industrial utilization of these processes (example DE 3832571, Journal of Organic Chemistry 1966, (31), 3473-3482 and Tetrahedron 2004, (60), 81-92).

In order to compensate for this disadvantage, in the past, a number of alternative processes for the preparation of aromatic formamides have been described. Thus, the reaction of aromatic amines with an excess of formic acid produces the corresponding formamides in high yields (DE 138839 and Bulletin of the Korean Chemical Society 2002, (23), 149-150). However, in this connection, on account of the considerable corrosivity of the formic acid, the apparatuses have to be manufactured from superior and therefore more expensive materials. Furthermore, the formic acid is obtained industrially through acidic hydrolysis of methyl formate. A direct use of methyl formate would thus constitute a more efficient and more cost-effective synthesis route.

The use of reactive esters of formic acid with, for example, 2,2,2-trifluoroethanol or pentafluorophenol permits high yields under mild conditions (Synthesis 1987, 510 and Organic Letters 2002, (4), 111-113). However, these reagents can only be used for industrial applications to a very limited degree since they are both expensive and also not available in large amounts.

The stoichiometric use of strong bases such as sodium hydride and lithium hexamethyldisilazide or phosphorous trichloride supported on silica gel likewise leads to efficient reactions (Organic Letters 2009, (11), 389-892, Organic Letters 2007, (9), 3631-3634 and Tetrahedron Letters 2005, (46), 7963-7966). However, a large amount of by-product is generated which has to be disposed of or recycled, which is costly.

To date, only a few syntheses of formamides from aromatic amines and formic acid alkyl esters in the presence of catalytically active compounds have been described. For this, firstly acids such as para-toluenesulfonic acid, trifluoroacetic acid or small amounts of formic acid have been used (Organic Letters 2006, (8), 1875-1878, Tetrahedron 2005, (61), 7144-7152, Journal of Organic Chemistry 1966, (31), 3473-3482 and Chemical Papers 1993, (47), 109-113). Daszkiewicz et al. (Chemical Papers 1993, (47), 109-113) describes for example the preparation of aromatic substituted formanilides by reacting ring-substituted anilines with n-butyl formate in the presence of trifluoroacetic acid as catalyst. The use of sodium methoxide or samarocenes has likewise been described (US 2005/0027120 and Journal of Organic Chemistry 1996, (61), 3088-3092). However, in these cases too, either the yields are too low for industrial application, expensive higher alkyl formates are used and/or the catalysts are very expensive or corrosive.

It was the object of the invention to develop a process that can be carried out industrially for the preparation of formamides from mono-, di- or polyfunctional aromatic amines which permits high space-time yields and selectivities even when using industrially accessible formic acid esters in the presence of a catalyst.

Surprisingly, it has been found that by reacting aromatic amines with an alkyl formate in the presence of a phosphorus-containing acid or of a Lewis-acidic metal salt, the desired formamides can be isolated in very good yields even after short reaction times.

The invention provides a process for the preparation of formamides by reacting aromatic amines with a formic acid ester in the presence of a catalyst, wherein the catalyst is a phosphorus-containing acid or a Lewis-acidic metal salt.

Examples of the phosphorus-containing acids (=proton donors) used in the process according to the invention are phosphorus(III) acids, such as $C_1$-$C_{10}$-alkyl-, preferably $C_1$-$C_4$-alkyl-, or $C_6$-$C_{14}$-aryl-, preferably $C_6$-$C_{10}$-arylphosphonic acids, if appropriate supported on a polymeric solid phase, and phosphorus(V) acids, such as ortho-phosphoric acid and higher condensates thereof (diphosphoric acid, metaphosphoric acid or polyphosphoric acid). In the case of the aforementioned phosphoric acids, some of the acid functions can be esterified with lower $C_1$-$C_4$-alcohols, such as for example methanol, ethanol or n-butanol. These phosphorus-containing acids can be used in pure form or as a mixture. Particular preference is given to using ortho-phosphoric acid in anhydrous or aqueous form.

Examples of the Lewis-acidic metal salts (=electron pair acceptors) used in the process according to the invention are corresponding salts of the transition metals, lanthanoids or metals of the 2nd, 3rd or 4th group or inorganic or organic acids. Preferably, the metal of the Lewis-acidic metal salt is selected from the group of: zinc, lead, tin, iron, aluminum, titanium, zirconium, scandium, yttrium, lanthanum, cerium or ytterbium. The aforementioned metal salts are generally the corresponding fluorides, chlorides, sulfates, nitrates, phosphates, carboxylates or sulfonates.

The carboxylates are generally the anions, formed by deprotonation, of carboxylic acids of the general formula $R(CO_2H)_n$. R here refers to $C_1$-$C_{18}$-alkyl radicals, $C_2$-$C_7$-alkenyl radicals, preferably ethenyl, $C_5$-$C_8$-cycloalkyl radicals, aromatic $C_6$-$C_{14}$-aryl radicals, preferably phenyl or naphthyl, or radicals of the naphthenic acids of the general structure (I)

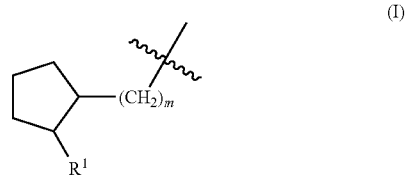

(I)

in which $R^1$ is a hydrogen or methylenecyclopentyl radical and m is zero or an integer from 1 to 12,
and n is an integer from 1 to 4. Preferably, n is 1.

Preference is given to carboxylates in which R is a $C_1$-$C_{10}$-alkyl radical, in particular $C_1$-$C_6$-alkyl radical, $C_5$-$C_8$-cycloalkyl radical or a naphthenic acid radical of the above structure (I). Particularly preferably, R is the radicals methyl, ethyl, propyl or cyclopentyl. All of the specified carboxylates can be used individually or as a mixture.

The sulfonates are generally to be understood as meaning optionally substituted $C_1$-$C_4$-alkyl-, in particular methyl- or ethyl-, $C_6$-$C_{10}$-aryl-, in particular phenyl- or tolyl-, or $C_{10}$-$C_{14}$-alkylbenzenesulfonates. The aforementioned alkyl radicals are preferably mono- or polysubstituted by halogen, in particular fluorine. Particular preference is given to trifluoromethanesulfonate.

The described Lewis-acidic metal salts also include the corresponding mono, di- or polyhydrates with water of crystallization.

The Lewis-acidic metal salts of zinc, lead, ytterbium, scandium or lanthanum, in particular carboxylates, sulfonates or nitrates thereof, are particularly preferred. Very particular preference is given to using zinc acetate, zinc acetate dihydrate, zinc naphthenate or ytterbium trifluoromethanesulfonate.

The catalyst is used in a molar ratio of from 0.001 to 0.3, preferably from 0.01 to 0.1, in each case based on the amino groups.

The formic acid ester is derived from a linear or branched aliphatic alcohol having 1 to 6 carbon atoms, such as methanol, ethanol, n-propanol, n-butanol, n-pentanol or n-hexanol, or from a linear or branched 1-alkenyl formate having 2-6 carbon atoms in the alkenyl radical, such as vinyl formate or isoprenyl formate. The aforementioned formic acid esters can be used individually or as a mixture. Preference is given to using linear or branched $C_1$-$C_6$-alkyl formates, particularly preferably methyl formate, which is also available on an industrial scale. Methyl formate is preferably prepared by reacting carbon monoxide with methanol.

The formic acid ester is used in a molar ratio of formic acid ester to amino groups of from 1:1 to 20:1, preferably from 1.5:1 to 8:1.

The reaction of the aromatic amine with the formic acid ester in the presence of the catalyst is preferably carried out at a reaction temperature of 20-160° C., particularly preferably 60-120° C. At this temperature, a quantitative conversion of the aromatic amine is obtained within 0.5-5 h, with reaction times of 2 h routinely being achieved. The pressure conditions are generally selected depending on the formic acid ester used and its boiling temperature. The reaction can be carried out at autogenous pressure (pressure which is established during the reaction in the closed vessel at the reaction temperature) or else also at a higher pressure of from 1 to 100 bar absolute or a subatmospheric pressure of from 0.001 to 1 bar absolute. Solvents which can be used are the formic acid ester itself or other inert compounds. Suitable solvents are, for example, amides such as N,N-dimethylformamide or N,N-dimethylacetamide, sulfoxides such as dimethyl sulfoxide, aromatic hydrocarbons with or without alkyl, halogen or alkoxy substituents such as toluene, the isomeric xylenes, mesitylene, ethylbenzene, chlorobenzene, the isomeric dichloro- or trichlorobenzenes, anisole, mono- or polyethers such as tetrahydrofuran, dioxane or dimethoxyethane, dialkyl ethylene glycols, such as, for example, diethylene glycol dimethyl ether and triethylene glycol dimethyl ether. These can be used individually or as a mixture.

In the process according to the invention, mono-, di- or polyfunctional aromatic amines are used. The aforementioned amines are primary or secondary amines of the general formula $R^2(NHR^3)_n$, in which $R^2$ is an optionally substituted $C_6$-$C_{34}$-aryl radical, preferably $C_6$-$C_{20}$-aryl radical, in particular $C_6$-$C_{14}$-aryl radical, and particularly preferably phenyl or tolyl or tolylene. $R^3$ is a $C_1$-$C_4$-alkyl radical, in particular methyl or ethyl radical, or a hydrogen atom and n is an integer from 1 to 3, preferably 1 or 2, per aromatic cycle. Preferably, $R^3$ is a hydrogen atom. Suitable substituents of the aryl radical are, for example, chlorine, fluorine, bromine, cyano, alkyl, alkoxy, alkylcarbonyl and/or alkoxycarbonyl, where alkyl and alkoxy generally have 1 to 10, preferably 1 to 6, particularly preferably 1 to 4, carbon atoms. Representatives from this group are, for example, aniline, o-, m- and/or p-toluidine, o-, m- and/or p-chloroaniline, o-, m- and/or p-bromoaniline, o-, m- and/or p-trifluoromethylaniline, 2,4-, 2,6-, 3,4- and/or 3,5-dimethyl-, -dichloro-, -dibromo- or -diethylaniline, p-tert-butylaniline, diaminotoluene (TDA), in particular 2,4- and/or 2,6-diaminotoluene, diaminodiphenylmethane (MDA), in particular 2,4"-diaminodiphenylmethane, 4,4"-diaminodiphenylmethane, 2,2"-diaminodiphenylmethane and/or higher homologues (polyphenylenepolymethylenepolyamines) or o-, m- and/or p-phenylenediamine. Preference is given to using aniline, the isomers of diaminotoluene, in particular 2,4- and 2,6-diaminotoluene, and/or the isomers and higher homologues of diaminodiphenylmethane.

Isolation of the aromatic formamides can take place in various ways known to the person skilled in the art. This may be for example a fractional distillation. Alternatively, the reaction discharge can be evaporated to dryness and the solid resulting therefrom can be purified by washing with or recrystallization from a suitable solvent. Furthermore, the product of value can be precipitated by adding a suitable solvent, isolated by filtration and purified by washing or recrystallization.

In one preferred embodiment of the process according to the invention for the preparation of formamides, the product of value is produced as early as during the reaction or only after the reaction is complete as solid suspended in excess reagent or solvent, which is then isolated by filtration. This can take place at reaction temperature or else following appropriate cooling to, for example, room temperature under autogenous pressure, atmospheric pressure or else increased pressure. The formamide is typically produced here in a form that is adequately pure for further processing, but, if necessary, can also be further purified by washing with formic acid esters or solvents. After separating the solid from the filtrate, the former can be isolated in solid form, as melt or else following dissolution in a suitable solvent and, where appropriate, be fed to a further reaction stage. From the filtrate, the excess reagent, the solvent possibly used in the reaction and the catalyst, individually or separately, can be isolated and be used in a further reaction cycle. Any residues of unreacted starting material present and/or intermediates (aminoformamides) formed during the reaction of polyamines can thus also be isolated and returned to the process. The process can be carried out either continuously or discontinuously.

The formamides obtained can, if they are derived from primary aromatic amines, be processed to industrially important aromatic isocyanates, for example by oxidative dehydrogenation.

The invention is illustrated in more detail in the examples below without limiting it thereto.

EXAMPLES

Example 1

10.0 g (81.9 mmol) of 2,4-diaminotoluene were dissolved in 40.0 g of N,N-dimethylacetamide and 49.2 g (819 mmol)

of methyl formate and admixed with 0.47 g (4.1 mmol) of 85% strength by weight aqueous ortho-phosphoric acid. The mixture was charged to a 300 ml autoclave and stirred for 4 h at 90° C. under autogenous pressure. After cooling to room temperature, the resulting mixture was evaporated to dryness. The resulting brownish solid (17.3 g) comprised, besides solvent residues and the catalyst, according to NMR spectroscopy, the bisformamide and the regioisomeric monoamides in a molar ratio of 97:3.

Example 2

10.0 g (81.9 mmol) of 2,4-diaminotoluene were dissolved in 40.0 g of N,N-dimethylacetamide and 49.2 g (819 mmol) of methyl formate and admixed with 2.54 g (4.1 mmol) of ytterbium(III) trifluoromethanesulfonate. The mixture was charged to a 300 ml autoclave and stirred for 4 h at 90° C. under autogenous pressure. After cooling to room temperature, the resulting mixture was evaporated to dryness. The resulting brownish solid (23.4 g) comprised, besides solvent residues and the catalyst, according to NMR spectroscopy, the bisformamide and the regioisomeric monoamides in a molar ratio of 94:6.

Example 3

10.0 g (81.9 mmol) of 2,4-diaminotoluene were dissolved in 40.0 g of N,N-dimethylacetamide and 49.2 g (819 mmol) of methyl formate and admixed with 0/5 g (4.1 mmol) of zinc(II) acetate. The mixture was charged to a 300 ml autoclave and stirred for 4 h at 90° C. under autogenous pressure. After cooling to room temperature, the resulting mixture was evaporated to dryness. The resulting brownish solid (16.4 g) comprised, besides solvent residues and the catalyst, according to NMR spectroscopy, the bisformamide and the regioisomeric monoamides in a molar ratio of 92:8.

Example 4

10.0 g (81.9 mmol) of 2,4-diaminotoluene were dissolved in 40.0 g of N,N-dimethylacetamide and 49.2 g (819 mmol) of methyl formate and admixed with 1.55 g (4.1 mmol) of lead(II) acetate. The mixture was charged to a 300 ml autoclave and stirred for 4 h at 90° C. under autogenous pressure. After cooling to room temperature, the resulting mixture was evaporated to dryness. The resulting brownish solid (15.7 g) comprised, besides solvent residues and the catalyst, according to NMR spectroscopy, the bisformamide and the regioisomeric monoamides in a molar ratio of 73:27.

Comparative Example 1

10.0 g (81.9 mmol) of 2,4-diaminotoluene were dissolved in 40.0 g of N,N-dimethylacetamide and 49.2 g (819 mmol) of methyl formate and admixed with 0.40 g (4.2 mmol) of methanesulfonic acid. The mixture was charged to a 300 ml autoclave and stirred for 4 h at 90° C. under autogenous pressure. After cooling to room temperature, the resulting mixture was evaporated to dryness. The resulting brown, high-viscosity oil (14.8 g) comprised, besides solvent residues and the catalyst, according to NMR spectroscopy, the bisformamide, the regioisomeric monoamides and 2,4-diaminotoluene in a molar ratio of 10:75:15.

Comparative Example 2

10.0 g (81.9 mmol) of 2,4-diaminotoluene were dissolved in 40.0 g of N,N-dimethylacetamide and 49.2 g (819 mmol) of methyl formate and admixed with 0.42 g (4.1 mmol) of 96% strength by weight aqueous sulfuric acid. The mixture was charged to a 300 ml autoclave and stirred for 4 h at 90° C. under autogenous pressure. After cooling to room temperature, the resulting mixture was evaporated to dryness. The resulting brown, high-viscosity oil (15.2 g) comprised, besides solvent residues and the catalyst, according to NMR spectroscopy, the bisformamide, the regioisomeric monoamides and 2,4-diaminotoluene in a molar ratio of 23:74:3.

Comparative Example 3

10.0 g (81.9 mmol) of 2,4-diaminotoluene were dissolved in 40.0 g of N,N-dimethylacetamide and 49.2 g (819 mmol) of methyl formate and admixed with 0.65 g (4.1 mmol) of phenylsulfonic acid. The mixture was charged to a 300 ml autoclave and stirred for 4 h at 90° C. under autogenous pressure. After cooling to room temperature, the resulting mixture was evaporated to dryness. The resulting brown, high-viscosity oil (15.6 g) comprised, besides solvent residues and the catalyst, according to NMR spectroscopy, the bisformamide, the regioisomeric monoamides and 2,4-diaminotoluene in a molar ratio of 12:76:12.

Comparative Example 4

10.0 g (81.9 mmol) of 2,4-diaminotoluene were dissolved in 40.0 g of N,N-dimethylacetamide and 49.2 g (819 mmol) of methyl formate and admixed with 1.57 g (4.1 mmol) of zirconium(IV) tert-butoxide. The mixture was charged to a 300 ml autoclave and stirred for 4 h at 90° C. under autogenous pressure. After cooling to room temperature, the resulting mixture was evaporated to dryness. The resulting brown, high-viscosity oil (15.4 g) comprised, besides solvent residues and the catalyst, according to NMR spectroscopy, the bisformamide, the regioisomeric monoamides and 2,4-diaminotoluene in a molar ratio of 41:58:1.

Comparative Example 5

10.0 g (81.9 mmol) of 2,4-diaminotoluene were dissolved in 40.0 g of N,N-dimethylacetamide and 49.2 g (819 mmol) of methyl formate. The mixture was charged without catalyst to a 300 ml autoclave and stirred for 12 h at 90° C. under autogenous pressure. After cooling to room temperature, the resulting mixture was evaporated to dryness. The resulting brown, high-viscosity oil comprised, besides solvent residues, according to NMR spectroscopy and thin-layer chromatography, no significant amounts of bisformamide, with only the regioisomeric monoamides and 2,4-diaminotoluene.

Example 5

10.0 g (81.9 mmol) of 2,6-diaminotoluene were dissolved in 40.0 g of N,N-dimethylacetamide and 49.2 g (819 mmol) of methyl formate and admixed with 0.47 g (4.1 mmol) of 85% strength by weight aqueous ortho-phosphoric acid. The mixture was charged to a 300 ml autoclave and stirred for 4 h at 90° C. under autogenous pressure. After cooling to room temperature, the resulting mixture was evaporated to dryness. The resulting brownish solid (14.6 g) comprised, besides solvent residues and the catalyst, according to NMR spectroscopy, the bisformamide and the monoamide in a molar ratio of 97:3.

Example 6

21.7 g (178 mmol) of 2,4-diaminotoluene were dissolved in 21.7 g of N,N-dimethylacetamide and 107 g (1.78 mol) of methyl formate and admixed with 1.02 g (8.8 mmol) of 85% strength by weight aqueous ortho-phosphoric acid. The mixture was charged to a 300 ml autoclave and stirred for 2 h at 90° C. under autogenous pressure. After cooling to room temperature, the resulting suspension was diluted with 70 g of methyl formate and filtered, and the virtually colorless solid was washed with 70 g of methyl formate and dried. In this way, 29.6 g (94%), according to thin-layer chromatography and NMR spectroscopy, of a pure bisformamide were isolated.

Example 7

21.7 g (178 mmol) of 2,4-diaminotoluene were dissolved in 128 g (2.13 mol) of methyl formate and admixed with 1.63 g (8.9 mmol) of zinc(II) acetate. The mixture was charged to a 300 ml autoclave and stirred for 2 h at 90° C. under autogenous pressure. After cooling to room temperature, the resulting suspension was diluted with 70 g of methyl formate and filtered, and the virtually colorless solid was washed with 70 g of methyl formate and dried. In this way, 29.8 g (94%), according to thin-layer chromatography and NMR spectroscopy, of a pure bisformamide were isolated.

Example 8

20.0 g (164 mmol) of 2,6-diaminotoluene were dissolved in 118 g (1.97 mol) of methyl formate and admixed with 5.01 g (8.0 mmol) of 65% strength by weight zinc(II) naphthenate in mineral oil (corresponds to a 10% strength by weight zinc solution). The mixture was charged to a 300 ml autoclave and stirred for 2 h at 90° C. under autogenous pressure. After cooling to room temperature, the resulting suspension was diluted with 70 g of methyl formate and filtered, and the virtually colorless solid was washed with 70 g of methyl formate and dried. In this way, 26.7 g (92%), according to thin-layer chromatography and NMR spectroscopy, of a pure bisformamide were isolated.

Example 9

21.7 g (178 mmol) of 2,4-diaminotoluene and 2,6-diaminotoluene in the ratio 80:20 were dissolved in 128 g (2.13 mol) of methyl formate and admixed with 1.02 g (8.8 mmol) of 85% strength by weight aqueous ortho-phosphoric acid. The mixture was charged to a 300 ml autoclave and stirred for 2 h at 90° C. under autogenous pressure. After cooling to room temperature, the resulting suspension was diluted with 70 g of methyl formate and filtered, and the virtually colorless solid was washed with 70 g of methyl formate and dried. In this way, 27.8 g (88%), according to thin-layer chromatography and NMR spectroscopy, of a pure mixture of the regioisomeric bisformamides were isolated.

Example 10

15.0 g (161 mmol) of aniline were dissolved in 60.0 g of N,N-dimethylacetamide and 48.5 g (808 mmol) of methyl formate and admixed with 1.07 g (4.9 mmol) of zinc(II) acetate dihydrate. The mixture was charged to a 300 ml autoclave and stirred for 2 h at 90° C. under autogenous pressure. After cooling to room temperature, the excess methyl formate and the methanol formed were distilled off. The resulting red-brown oil comprised, besides relatively large amounts of solvent and the catalyst, according to NMR spectroscopy, only formanilide and aniline in a molar ratio of 99:1.

Example 11

15.0 g (161 mmol) of aniline were dissolved in 60.0 g of N,N-dimethylacetamide and 48.5 g (808 mmol) of methyl formate and admixed with 0.56 g (4.9 mmol) of 85% strength by weight aqueous ortho-phosphoric acid. The mixture was charged to a 300 ml autoclave and stirred for 2 h at 90° C. under autogenous pressure. After cooling to room temperature, the excess methyl formate and the methanol formed were distilled off. The resulting red-brown oil comprised, besides relatively large amounts of solvent and the catalyst, according to NMR spectroscopy, only formanilide and aniline in a molar ratio of 98:2.

The examples show that aromatic formamides are obtainable by the process according to the invention in high selectivities and high space-time yields. The products are formed in high purity, meaning that no complex post-purification is required.

The invention claimed is:

1. A process for preparing a formamide, comprising reacting an aromatic amine with a formic acid ester in the presence of a catalyst, wherein the catalyst is a phosphorus-comprising acid or a Lewis-acidic metal salt, wherein a metal of the Lewis-acidic metal salt is selected from the group consisting of zinc, lead and ytterbium.

2. The process of claim 1, wherein the catalyst is ortho-phosphoric acid or a higher condensate of ortho-phosphoric acid.

3. The process of claim 1, wherein the catalyst is a Lewis-acidic metal salt, and the Lewis-acidic metal salt is a carboxylate, sulfonate or nitrate of zinc, lead or ytterbium.

4. The process of claim 1, wherein the catalyst is a Lewis-acidic metal salt selected from the group consisting of zinc acetate, zinc acetate dihydrate, zinc naphthenate and ytterbium trifluoromethanesulfonate.

5. The process of claim 1, wherein the catalyst is employed in a molar ratio of 0.001 to 0.3, based on amino groups.

6. The process of claim 1, wherein the formic acid ester is a linear or branched $C_1$-$C_6$-alkyl formate or $C_2$-$C_{61}$-alkenyl formate.

7. The process of claim 1, wherein the formic acid ester is methyl formate.

8. The process of claim 1, wherein the formic acid ester is employed in a molar ratio of formic acid ester to amino groups of from 1:1 to 20:1.

9. The process of claim 1, wherein the aromatic amine is a primary or secondary amine having a general formula $R^2(NHR^3)_n$, in which $R^2$ is an optionally substituted $C_6$-$C_{34}$-aryl radical, $R^3$ is a $C_1$-$C_4$-alkyl radical or a hydrogen atom and n is an integer of 1 to 3 per aromatic cycle.

10. The process of claim 1, wherein the aromatic amine is a primary amine.

11. The process of claim 1, wherein the aromatic amine is at least one selected from the group consisting of aniline, a diaminotoluene, a diaminodiphenylmethane, and a polyphenylenepolymethylenepolyamine.

12. The process of claim 1, wherein a suspension-like reaction discharge is filtered, and the formamide is isolated as a solid.

13. The process of claim 1, further comprising reusing, recycling, or both reusing and recycling (i) a catalyst present in a filtrate and any solvent present, (ii) an excess of formic acid ester, (iii) a starting material residue and (iv) an aminoformamide, individually or separately, in a further reaction cycle.

14. The process of claim 1, wherein the catalyst is a phosphorus-comprising acid selected from the group consisting of ortho-phosphoric acid, diphosphoric acid, metaphosphoric acid, and polyphosphoric acid.

15. The process of claim 1, wherein $R^2$ is selected from the group consisting of phenyl, tolyl and tolylene.

16. The process of claim 1, wherein $R^3$ is selected from the group consisting of methyl, ethyl and hydrogen.

17. The process of claim 1, wherein the aromatic amine is at least one selected from the group consisting of 2,4-diaminotoluene, 2,6-diaminotoluene, 2,4'-diaminodiphenylmethane, 4,4'-diaminodiphenylmethane, and 2,2'-diaminodiphenylmethane.

18. The process of claim 1, wherein:
the aromatic amine is 2,4-diaminotoluene;
the formic acid ester is methyl formate; and
the catalyst is selected from the group consisting of ortho-phosphoric acid, ytterbium(III) trifluoromethanesulfonate, zinc(II) acetate and lead(II) acetate.

19. The process of claim 1, wherein:
the aromatic amine is 2,4-diaminotoluene, 2,6-diaminotoluene, or a mixture of both;
the formic acid ester is methyl formate; and
the catalyst is ortho-phosphoric acid or zinc(II) naphthenate.

20. The process of claim 1, wherein:
the aromatic amine is aniline;
the formic acid ester is methyl formate; and
the catalyst is ortho-phosphoric acid or zinc(II) acetate dihydrate.

* * * * *